United States Patent [19]
Noda et al.

[11] Patent Number: 4,698,306
[45] Date of Patent: Oct. 6, 1987

[54] PROCESS FOR PRODUCING PEROXIDASE
[75] Inventors: Satoko Noda, Kyoto; Matsui Susumu, Ootsu, both of Japan
[73] Assignee: Takara Shuzo Co., Ltd., Kyoto, Japan
[21] Appl. No.: 792,731
[22] Filed: Oct. 28, 1985
[30] Foreign Application Priority Data
Nov. 28, 1984 [JP] Japan ................................ 59-250900
[51] Int. Cl.$^4$ .......................... C12N 9/08; C12Q 1/28; C12R 1/645
[52] U.S. Cl. .................................... 435/192; 435/28; 435/911
[58] Field of Search .................................. 435/192, 28

[56] References Cited
U.S. PATENT DOCUMENTS
4,328,312  5/1982  Tsurumi et al. ..................... 435/192

FOREIGN PATENT DOCUMENTS
57-99192   6/1982  Japan ................................. 435/192
59-179075 10/1984  Japan ................................. 435/192

Primary Examiner—Lionel M. Shapiro
Attorney, Agent, or Firm—Wenderoth, Lind & Ponack

[57] ABSTRACT

Process for producing peroxidase by cultivating Coprinus macrorhizus K-1330 (FERM BP-648).

2 Claims, 5 Drawing Figures

PROCESS FOR PRODUCING PEROXIDASE

The present invention relates to a process for producing peroxidase. More particularly, it relates to a process for producing peroxidase from a culture broth produced by the cultivation of a fungus belonging to the class Basidiomycetes.

In general, peroxidase is widely distributed in plants and is present in large quantities in horseradish, figs, Japanese radish, etc. At present, peroxidase is commercially produced from horseradish because the peroxidase content of the root of horseradish is highest, and it finds wide application as a clinical diagnostic reagent, for example, for quantitative determination of glucose, total cholesterol, etc. in blood serum in combination with various oxidases, or as a labelled enzyme in enzyme immunoassay. As the peroxidase of microorganism origin, there are given cytochrome C peroxidase, NADH peroxidase, etc. produced by bacteria and molds. But, these peroxidases are different in action from those of plant origin such as peroxidase from horseradish, etc., so that they cannot be used as a clinical diagnostic reagent.

In recent years, it was reported that microorganisms belonging to the genera Alternaria, Cochliobolus, Pellicularia and Curvularia (Japanese Patent Kokai No. 99192/1982) and the genus Bacillus (ibid., No. 179488/1983) produce peroxidase which can be used as a clinical diagnostic reagent. But, these strains produce only small amounts of peroxidase, so that they are unfavorable to commercial production.

In view of these facts, the present inventors screened many strains of Basidiomycetes for peroxidase production and as a result, found that a certain microorganism of the class Basidiomycetes will produce peroxidase having excellent properties usable as a clinical diagnostic reagent in large amounts in its culture broth. The inventors thus completed the present invention.

An object of the present invention, therefore, is to provide a process for producing peroxidase usable as a clinical diagnostic reagent at commercially low costs by cultivating a strain belonging to the class Basidiomycetes.

Briefly, the present invention provides a process for producing peroxidase which comprises cultivating a peroxidase-producing microorganism belonging to the genus Coprinus in a culture medium and collecting the peroxidase produced from the resulting culture broth.

The peroxidase obtained by the method of the present invention has an action to catalyze the color-development of hydrogen-donative chromogens such as 4-aminoantipyrine (hereinafter referred to as 4-AA)/-phenol system, 4-AA/dimethylaniline system, 4-AA/N-ethyl-N-hydroxyethyl-m-toluidine (hereinafter referred to as EHMT) system and 3-methyl-2-benzothiazolinonehydrazone (hereinafter referred to as MBTH) system, in the presence of hydrogen peroxide. This peroxidase, therefore, can be used as a clinical diagnostic reagent.

The microorganisms belonging to the class Basidiomycetes used in the present invention include strains belonging to the genus Coprinus of the family Coprinaceae such as *Coprinus macrorhizus* K-1330.

This strain was isolated from the fruiting body grown gregariously on cow's dung in Ootsu City, Shiga Prefecture, Japan and the physical characteristics of the fruiting body and spores thereof are as follows:

Cap 2-5 cm broad, 1.5-4.5 cm high, in its immature stage cylindrical to conical, and then bell-shaped. At first, the surface is grey and covered with pure white soft hairs, then they drop and the surface becomes smooth. The cap is furrowed radially from the apex to the margin, and at the margin it is irregularly rugged. During growth, the gills roll upward and start to dissolve. Gills dense.

Stem 3-10 cm high, white. The substratum swollen and prolonged finely as a pseudorhiza (3-5 cm long).

Spores ellipsoid, smooth, $11-15 \times 6-8\mu$. Spore print black. Habitat on mature-heaps and cattle-dung.

This strain has been deposited at Fermentation Research Institute, Agency of Industrial Science and Technology, Japan under the deposit number FERM BP-648.

The invention will be explained in more detail as follows by referring partly to the accompanying drawings wherein:

FIG. 1 a graph to show the activity-pH relationship of the peroxidase obtained by the present invention.

Figure 1:
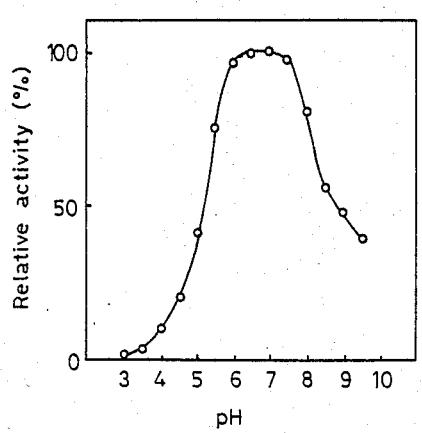

Referring now to the method of the present invention in more detail, any well-known nutrient source may be added to the culture medium, if the strain used can utilize it to produce peroxidase. As the carbon source, for example glucose, starch, sucrose, maltose, lactose, glycerol, dextrin, oils and fats and the like may be used. As the nitrogen source, yeast extract, peptone, defatted soybean, corn steep liquor, meat extract and the like are suitable. Also, inorganic substances and metal salts such as phosphates, potassium salts, magnesium salts and the like may be added. Particularly, the addition of an iron salt (e.g. iron sulfate, iron chloride, iron nitrate, etc.) is desirable as the production of the peroxidase is greatly increased thereby. The amount of such iron salt is generally 0.01%–0.50% (w/v), preferably 0.08–0.20% (w/v).

In cultivating the strain belonging to the genus Coprinus, the output of peroxidase varies largely depending upon the culture conditions. Generally, the culture temperature is preferably 20° to 35° C., the pH of the culture medium is preferably 4 to 8 and the production of the peroxidase reaches maximum by aeration/stirring culture for 4 to 12 days. In this case, it is natural that the culture condition should be determined so as to obtain a maximum output of the peroxidase according to the particular strain and medium composition employed. The peroxidase produced by the organisms of the present invention is present mainly in the filtrate of the culture broth, and it is separated as precipitate by adding 20 to 80 w/v% of a precipitating agent (e.g. ammonium sulfate) or 50 to 80 w/v% of an organic solvent (e.g. alcohol, acetone) to the filtrate of the culture broth. The precipitate obtained is desalted by ultrafiltration, dialysis or Sephadex treatment to obtain a crude enzyme solution. For purifying the crude enzyme solution obtained, the solution is treated as follows: The solution is adsorbed to a column of DEAE-Sepharose CL-6B previously buffered with 0.01M phosphate buffer (pH, 7.0), and the adsorbed matter is washed with 0.02M phosphate buffer (pH, 7.0) and eluted with 0.1M phosphate buffer (pH, 7.0) to collect an active fraction. This active fraction is then concentrated and desalted by ultrafiltration, re-adsorbed to a column of DEAE-Sepharose CL-6B buffered with 0.01M phosphate buffer (pH, 7.0), and the adsorbed matter is washed with 0.02M phosphate buffer (pH, 7.0) and eluted with 0.05M phosphate buffer (pH, 7.0) to collect an active fraction. This active fraction is then dialyzed against distilled water and lyophilized to obtain a purified enzyme powder. This enzyme powder shows a single band by polyacrylamide gel disc electrophoresis.

The enzymological and physicochemical properties of the peroxidase of the present invention are as follows:

(1) Action:

This enzyme acts on hydrogen peroxide very specifically, to catalyze the oxidation of various compounds which may become hydrogen donors in the presence of hydrogen peroxide. The reaction mechanism is as follows:

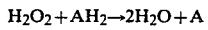

$$H_2O_2 + AH_2 \rightarrow 2H_2O + A$$

wherein $AH_2$ represents a hydrogen donor and A represents an oxidized hydrogen donor.

(2) Specificity for hydrogen donors:

The specificity of this enzyme for hydrogen donors prepared by combining 4-AA with various compounds was examined (Table 1).

TABLE 1

| Compound | Wavelength (nm) used in measurement | Relative activity (%) |
|---|---|---|
| Phenol | 500 | 100 |
| Resorcinol | " | 10 |
| Pyrocatechol | " | 58 |
| Hydroquinone | " | 10 |
| α-Naphthol | " | 18 |
| 2,4-Dibromophenol | 520 | 47 |
| 2,4-Dichlorophenol | " | 115 |
| 2,6-Dichlorophenol | " | 154 |
| 2,4,6-Trichlorophenol | " | 96 |
| Dimethylaniline | 550 | 21 |
| Diethylaniline | " | 49 |
| EHMT | " | 62 |

Also, the specificity of this enzyme for hydrogen donors prepared by combining MBTH with dimethylaniline, diethylaniline or EHMT was examined (Table 2). In this test, the activity value of 4-AA/phenol, the hydrogen donor used as a control, was taken to be 100.

TABLE 2

| Compound | Wavelength (nm) used in measurement | Relative activity (%) |
|---|---|---|
| Dimethylaniline | 590 | 50 |
| Diethylaniline | " | 49 |
| EHMT | " | 41 |
| (4-AA/phenol | 500 | 100) |

Figure 2:
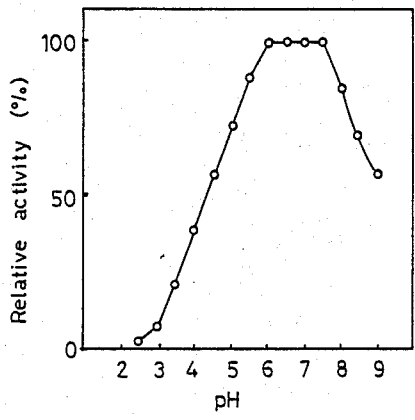
FIG. 2 shows the activity-pH relationship of this enzyme after being treated at 37° C. for 60 minutes and at different pH values.

(3) Optimum pH and pH stability:

This enzyme has a high activity in the vicinity of a pH of 7.0 as shown in the graph of FIG. 1. An acetate buffer solution was used for a pH of 3 to 3.5, a phosphate buffer solution for a pH of 6 to 8.5 and a borate buffer solution for a pH of 9 to 9.5. The pH stability of this enzyme when the enzyme was treated at 37° C. for 60 minutes and at different pH values is shown in FIG. 2. As apparent from FIG. 2, this enzyme is stable between pH 6.0 and pH 7.5.

Figure 3:
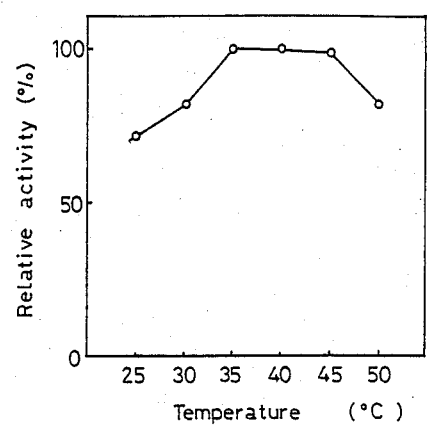
FIG. 3 shows the activity-temperature relationship of this enzyme.
Figure 4:
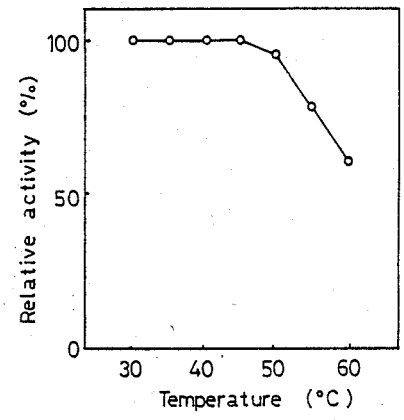
FIG. 4 shows the activity-temperature relationship of this enzyme after being treated at pH=7.0 for 10 minutes and at different temperatures.

(4) Optimum temperature and thermostability:

This enzyme has an optimum temperature in the vicinity of 35° to 40° C. as shown in the graph of FIG. 3. The thermostability of this enzyme when it was treated for 10 minutes at a pH of 7.0 and at different temperatures is shown in FIG. 4. This enzyme is stable up to 45° C.

(5) Molecular weight:

The molecular weight of this enzyme is about 37,000 by the gel filtration method with Sephacryl S-200 (produced by Pharmacia) and about 41,000 by the SDS-polyacrylamide gel electrophoretic method.

(6) Homogeneity:

Disc electrophoresis was done using a 7.5% polyacrylamide gel (pH, 9.4) and the protein was stained. One stained band of protein is noticed. A single band is also noticed by SDS-polyacrylamide gel electrophoresis.

(7) Isoelectric point:

The isoelectric point of this enzyme measured by the isoelectric focusing method with Pharmalyte (pH, 3–10; produced by Pharmacia) is 3.4 to 3.5.

(8) Effects of inhibitors, metal ions and metal chelating agents:

This enzyme is inhibited by $Hg^{2+}$, potassium cyanide, sodium azide, thiourea, etc. (Table 3).

TABLE 3

| Additive (1 mM) | Relative activity (%) | Additive (1 mM) | Relative activity (%) |
|---|---|---|---|
| No addition | 100 | Iodoacetic acid | 100 |
| L-cysteine | 105 | EDTA | 97 |
| Dithiothreitol | 95 | $CuSO_4$ | 105 |
| Thiourea | 57 | $MnCl_2$ | 86 |
| Potassium cyanide | 22 | $FeCl_3$ | 107 |
| Sodium azide | 52 | $BaCl_2$ | 96 |
| PCMB* | 98 | $CoCl_2$ | 98 |
| PMSF** | 98 | $ZnCl_2$ | 85 |
| Sodium fluoride | 103 | $SnCl_2$ | 92 |
| Sodium sulfide | 82 | $NiSO_4$ | 92 |
| α,α'-Dipyridyl | 103 | $HgCl_2$ | 6 |
| o-Phenanthroline | 88 | | |

Figure 5:
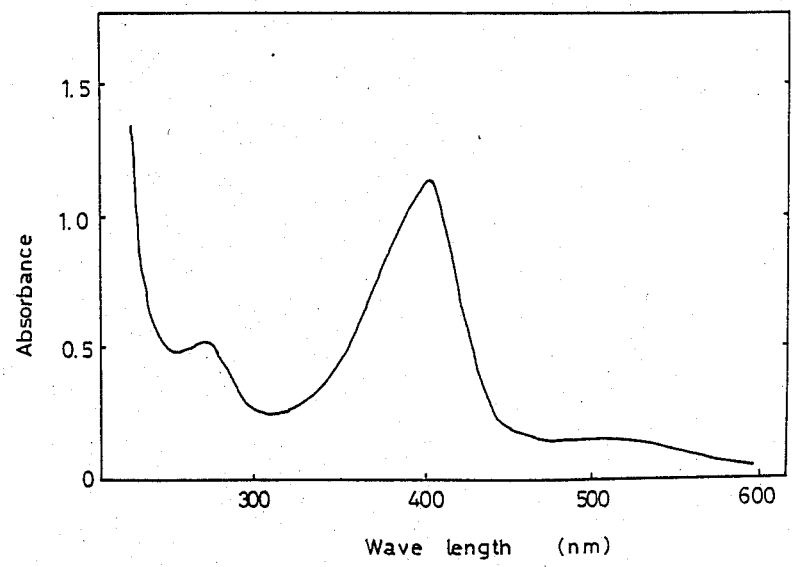
FIG. 5 shows the visible absorption spectrum of this enzyme (enzyme concentration, 0.057%; pH, 7.0).

*p-Chloromercuribenzoic acid
**Phenylmethylsulfonyl fluoride (9) Visible absorption spectrum:

This spectrum is shown in FIG. 5.

(10) Measurement of enzymatic activity:

The peroxidase activity was measured on the 4-AA/phenol system used in clinical diagnosis as a hydrogen donor. That is, reaction was carried out at 37° C. for 60 seconds using 3.0 ml of a reaction solution comprising 0.1 ml of 5 mM hydrogen peroxide solution, 1.0 ml of 0.3M phosphate buffer (pH, 7.0), 0.1 ml of 24.6 mM 4-AA solution, 0.1 ml of 0.42M phenol solution, 1.6 ml of water and 0.1 ml of the enzyme solution properly diluted, and the absorbance at 500 nm was measured ($OD_{sample}$). Separately, 0.1 ml of water was added as a control in place of the hydrogen peroxide solution, the absorbance was measured in the same manner as above ($OD_{blank}$), and a difference between $OD_{sample}$ and $OD_{blank}$, $\Delta OD_{500}$, was obtained. the peroxidase activity is calculated by the following equation:

$$\text{Unit/ml} = \frac{\Delta OD_{500}(OD_{sample} - OD_{blank}) \times Vt \times df}{6.17 \times t \times Vs}$$

-continued $$= \Delta OD_{500} \times 4.86 \times df$$

Vt: Volume of reaction solution (3.0 ml),
Vs: Volume of enzyme solution (0.1 ml),
6.17: Molecular extinction coefficient per millimole of a quinoneimine dye at 500 nm (cm$^2$/micromole),
t: Reaction time (1 minute),
df: Rate of dilution.

EXPERIMENTAL EXAMPLE

Effect of iron salts on the production of peroxidase

One hundred milliliters of a medium containing 2% of glucose, 0.3% of yeast extract, 1% of peptone, 0.3% of KH$_2$PO$_4$ and 0.1% of MgSO$_4$.7H$_2$O was added to each of 500-ml Erlenmeyer flasks, and FeSO$_4$.7H$_2$O was added to the flasks so that its respective concentrations were 0%, 0.04%, 0.08%, 0.12%, 0.16%, 0.20%, 0.24% and 0.32%. After sterilization at 120° C. for 20 minutes, the flasks were cooled, inoculated with *Coprinus macrorhizus* K-1330 (FERM BP-648), cultivated at 26° C. for 5 to 10 days with stirring at a rate of 100 rpm and sampled occasionally. The culture broths thus obtained were filtered to remove mycelia, and the peroxidase activity (maximum activity) of each filtrate obtained was measured. The result is shown in Table 4.

TABLE 4

| Amount of FeSO$_4$.7H$_2$O added (%) | Peroxidase activity (maximum activity, unit/ml) |
|---|---|
| No addition | 19.4 |
| 0.04 | 28.0 |
| 0.08 | 46.4 |
| 0.12 | 75.5 |
| 0.16 | 80.2 |
| 0.20 | 66.0 |
| 0.24 | 36.8 |
| 0.32 | 17.0 |

As apparent from Table 4, the output of the peroxidase was remarkably increased by adding the iron salt to the medium. Hereupon, the optimum concentration of FeSO$_4$.7H$_2$O is 0.12 to 0.20%.

A method for producing the peroxidase according to the present invention will be illustrated hereinafter with reference to the following examples, but the present invention is not limited to these examples.

EXAMPLE 1

A slant medium containing 2% of glucose, 0.5% of Ebios and 1.5% of agar (Ebios medium) was inoculated with *Coprinus macrorhizus* K-1330 (FERM BP-648) and cultivated while kept still at 25° C. for one week to obtain a seed culture. Separately from this, 100 ml of a medium containing 2% of glucose, 0.3% of yeast extract, 1% of peptone, 0.3% of KH$_2$PO$_4$ and 0.1% of MgSO$_4$.7H$_2$O was added to a 500-ml Erlenmeyer flask, and after being sterilized at 120° C. for 20 minutes, it was then cooled and inoculated with the above seed culture. Thereafter, cultivation was carried out at 27° C. for 10 days with stirring at a rate of 100 rpm. After completion of the cultivation, the mycelium was removed by filtration to obtain a filtrate. The peroxidase activity of this filtrate was 20.0 units/ml.

EXAMPLE 2

One hundred milliliters of a medium containing 2% of glucose, 0.3% of yeast extract, 1% of peptone, 0.3% of KH$_2$PO$_4$ and 0.1% of MgSO$_4$.7H$_2$O, as previously added to a 500-ml Erlenmeyer flask and sterilized at 120° C. for 20 minutes, was inoculated with *Coprinus macrorhizus* K-1330 (FERM BP-648) cultivated in the Ebios medium of Example 1, and cultivated at 26° C. for 7 days to obtain a seed culture broth. Separately from this, 20 liters of a medium containing 2% of glucose, 0.3% of yeast extract, 1% of peptone, 0.3% of KH$_2$PO$_4$, 0.1% of MgSO$_4$.7H$_2$O, 0.005% of CuSO$_4$.5H$_2$O and 0.02% of a defoaming agent (CB-442; produced by Nippon Yushi Co.) was added to a 30-liter jar fermentor and sterilized at 120° C. for 20 minutes. After cooling, the medium was inoculated with 100 ml of the above seed culture broth and cultivated at 26° C. for 6 days under the condition that the aeration rate was 13 liters per minute and the stirring rate was 270 revolutions per minute. After completion of the cultivation, the mycelium was removed by filtration to obtain a filtrate. The peroxidase activity of the filtrate was 41.5 units/ml. Ammonium sulfate was then added to 17 liters of this filtrate to give 80% saturation, and after allowing to stand for a whole day and night, the resulting precipitate was dissolved in about 500 ml of 0.01M phosphate buffer (pH, 7.0). The crude enzyme solution thus obtained was concentrated and desalted by ultrafiltration and adsorbed to a column [5.0 cm (diameter)×4 cm (length)] of DEAE-Sepharose CL-6B previously buffered with 0.01M phosphate buffer (pH, 7.0). The column was washed with 0.02M phosphate buffer (pH, 7.0) and eluted with 0.1M phosphate buffer (pH, 7.0) to collect an active fraction. This active fraction was then concentrated and desalted by ultrafiltration and re-adsorbed to a column [(2.5 cm (diameter)×4 cm (length)] of DEAE-Sepharose CL-6B buffered with 0.01M phosphate buffer (pH, 7.0). The column was washed with 0.02M phosphate buffer (pH, 7.0) and eluted with 0.05M phosphate buffer (pH, 7.0) to collect an active fraction. The active fraction thus obtained was dialyzed against distilled water and lyophilized to obtain 494 mg of a purified enzyme powder. The specific activity of this powder was 1180 units/mg. This enzyme powder showed a single band by polyacrylamide gel disc electrophoresis. The purification steps described above are shown in Table 5.

TABLE 5

| | Total protein content (mg) | Total activity (unit) | Specific activity (unit/mg) | Yield (%) |
|---|---|---|---|---|
| Culture filtrate | 237500 | 707000 | 2.98 | 100 |
| Salting-out with ammonium sulfate | 41200 | 724000 | 17.6 | 102 |
| Ultrafiltration | 17000 | 703000 | 41.4 | 99.4 |
| First DEAE-Sepharose CL-6B treatment | 1440 | 699000 | 485 | 98.9 |
| Second DEAE-Sepharose CL-6B treatment | 494 | 583000 | 1180 | 82.5 |

EXAMPLE 3

One hundred milliliters of a medium containing 2% of glucose, 0.3% of yeast extract, 1% of peptone, 0.3% of KH$_2$PO$_4$, 0.1% of MgSO$_4$.7H$_2$O and 0.16% of FeSO$_4$.7H$_2$O, as previously added to a 500-ml Erlenmeyer flask and sterilized at 120° C. for 20 minutes, was inoculated with *Coprinus macrorhizus* K-1330 (FERM BP-648) that has been cultivated in the Ebios medium of Example 1, and the new culture was cultivated at 26° C. for 10 days with stirring at a rate of 100 rpm. After completion of the cultivation, the mycelium was removed by filtration to obtain a filtrate. The peroxidase activity of this filtrate was 79.4 units/ml.

What we claim is:

1. A process for producing peroxidase which comprises cultivating *Coprinus macrorhizus* K-1330 (FERM BP-648) in a culture medium and collecting the peroxidase produced from the resulting culture broth.

2. A process as claimed in claim 1 wherein the cultivation is carried out in a culture medium containing an iron salt.

* * * * *